United States Patent [19]

Szczepanski

[11] Patent Number: 4,532,732
[45] Date of Patent: * Aug. 6, 1985

[54] OXIME DERIVATIVES FOR PROTECTING PLANT CROPS

[75] Inventor: Henry Szczepanski, Wallbach, Switzerland

[73] Assignee: Ciba Geigy Corporation, Ardsley, N.Y.

[*] Notice: The portion of the term of this patent subsequent to Feb. 5, 2002 has been disclaimed.

[21] Appl. No.: 344,708

[22] Filed: Feb. 1, 1982

Related U.S. Application Data

[60] Continuation-in-part of Ser. No. 238,345, Feb. 26, 1981, Pat. No. 4,468,242, which is a division of Ser. No. 69,414, Aug. 24, 1979, Pat. No. 4,269,775.

[30] Foreign Application Priority Data

Sep. 1, 1978 [CH] Switzerland .......................... 9252/78

[51] Int. Cl.$^3$ ............................................ A01N 25/32
[52] U.S. Cl. .......................... 47/57.6; 71/88; 71/93; 71/105; 71/108; 71/116; 71/118
[58] Field of Search .............................. 71/88, 105, 93; 47/57.6

[56] References Cited

U.S. PATENT DOCUMENTS

| | | | |
|---|---|---|---|
| 3,131,509 | 5/1964 | Hoffmann | 47/1 |
| 4,070,389 | 1/1978 | Martin | 260/465 E |
| 4,152,137 | 5/1979 | Martin | 71/105 |
| 4,269,775 | 5/1981 | Szczepanski et al. | 71/88 |
| 4,347,372 | 8/1982 | Fory et al. | 548/217 |

FOREIGN PATENT DOCUMENTS 515449 9/1979 Australia .

Primary Examiner—Catherine L. Mills
Attorney, Agent, or Firm—Edward McC. Roberts; Frederick H. Rabin

[57] ABSTRACT

The invention relates to novel oxime ethers of the formula

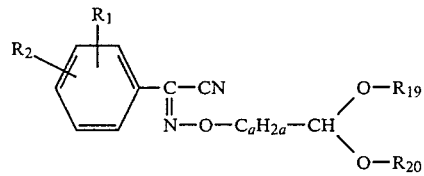

$R_1$ is hydrogen, methyl, methoxy, chlorine, cyano or trifluoromethyl, $R_2$ is hydrogen or chlorine, or $R_1$ and $R_2$ taken together is —CH=CH—CH=CH— attached to adjacent carbon atoms in the ring, a is 1 or 2, and $R_{19}$ and $R_{20}$ are each methyl or ethyl, or $R_{19}$ and $R_{20}$ taken together is $C_2$-$C_7$ alkylene having 2 or 3 carbon atoms in its principal chain, to their various uses as antidotes for herbicides and to compositions containing them. The invention also relates to plant seed treated with said antidotes.

169 Claims, No Drawings

OXIME DERIVATIVES FOR PROTECTING PLANT CROPS

CROSS REFERENCE TO RELATED APPLICATIONS

This is a continuation-in-part of application Ser. No. 238,345 filed on Feb. 26, 1981, now U.S. Pat. No. 4,468,242, which is a division of application Ser. No. 69,414 filed on Aug. 24, 1979, now U.S. Pat. No. 4,269,775.

BACKGROUND OF THE INVENTION

The present invention relates to novel oxime ethers, to their various uses as antidotes (safeners) for herbicides which damage certain cultivated plants so that such herbicides can be employed as selective herbicides, without loss of their herbicidal action against weeds, in crops of these cultivated plant. The invention relates also to compositions containing said oxime ethers, optionally together with a herbicide. The invention relates also to seed that has been treated with said oxime ethers.

It is known that herbicides of the most varied classes of substances, such as s-triazines, 1,2,4-triazinones, phenylurea derivatives, carbamates, thiolcarbamates, phenoxyacetates, phenoxypropionates, haloacetanilides, halophenoxyacetates, substituted phenoxyphenoxyacetates and phenoxyphenoxypropionates and benzoic acid derivatives have in the case of certain cultivated plants an action that is not selective or insufficiently selective, with the result that these herbicides attack not only the weeds to be combatted but to a lesser or greater extent also the cultivated plants.

Various substances have already been suggested for overcoming this problem, which substances are able to specifically antagonise the harmful action of the herbicide on the cultivated plant, i.e. to protect the cultivated plant without noticeably affecting the herbicidal action on the weeds to be combatted.

Thus, British Pat. No. 1,277,557 describes the protective treatment of seed and of shoots of wheat and sorghum with certain oxamic acid esters and amides in order to avoid the harm caused by alachlor (N-methoxymethyl-2,6-diethyl-chloroacetanilide). According to other references (German Offenlegungsschriften Nos. 1,952,910, 2,245,471 and French Pat. No. 2,021,611), antidotes are suggested for the treatment of cereals, maize seed and rice seed for protection against the attack from herbicidal thiolcarbamates. In German Pat. No. 1,576,676 and U.S. Pat. No. 3,131,509, there are suggested hydroxyaminoacetanilides and hydantoins for the protection of the seed of cereals against carbamates such as isopropyl N-phenylcarbamate, isopropyl m-chlorocarbanilate, etc. In U.S. Pat. Nos. 3,996,043 and 3,998,621, there are described certain antidotes for use with triazine herbicides which permit the herbicides to be used in cotton cultures.

It is a principal object of this invention to provide an antidote (safener) compound which will permit the use of chloroacetanilide herbicides and other effective weed killers in cultivated crops, particularly sorghum and rice.

DETAILED DISCLOSURE

The present invention relates to a method of protecting plant crops from the phytotoxic action of potent herbicides by means of a novel oxime ether derivative, also to compositions containing said oxime ether and also to propagation material of plants, such as seed, that has been treated with said oxime ether derivative.

The oxime derivative employed as antidote (safener) compound is of the formula I $$\text{(I)}$$

wherein $R_1$ is hydrogen, methyl, methoxy, chlorine, cyano or trifluoromethyl, $R_2$ is hydrogen or chlorine, or $R_1$ and $R_2$ taken together is —CH=CH—CH=CH— attached to adjacent carbon atoms in the ring, $a$ is 1 or 2, and $R_{19}$ and $R_{20}$ are each methyl or ethyl, or $R_{19}$ and $R_{20}$ taken together is $C_2$-$C_7$ alkylene having 2 or 3 carbon atoms in its principal chain.

Compounds of the formula I wherein $R_1$ is hydrogen and $R_2$ is hydrogen or chlorine represent a special objective of the invention.

The compounds of the formula I can be obtained by reacting an oxime derivative of the formula II $$\text{(II)}$$

with a compound of the formula III $$\text{Hal-}C_aH_{2a}\text{—CH} \begin{matrix} \diagup O-R_{19} \\ \diagdown O-R_{20} \end{matrix} \quad \text{(III)}$$

wherein $R_1$, $R_2$, $a$, $R_{19}$ and $R_{20}$ have the meanings given for formula I, Hal is halogen, preferably chlorine or bromine, and Me is hydrogen or a metal cation, preferably the cation of an alkali metal or alkaline earth metal.

The reactions can be carried out in the presence or absence of solvents which are inert to the reactants. Examples of suitable solvents are:

alcohols, such as ethanol; ketones, such as acetone; nitriles, such as acetonitrile; N,N-dialkylated amides, such as dimethyl formamide; dimethyl sulfoxide; pyridine; as well as mixtures of these solvents with one another.

Where Me is hydrogen, the process is carried out in the presence of a base. Examples of suitable bases are inorganic bases, such as the oxides, hydroxides, hydrides, carbonates and bicarbonates of alkali metals and alkaline earth metals, as well as e.g. tertiary amines, such as trialkylamines (e.g. triethylamine), and pyridine. The reaction temperatures are in the range between 0° and 150° C. The reactions are carried out under normal pressure and optionally in a nitrogen atmosphere.

The compounds of the formula II are prepared by methods analogous to known ones.

Compounds of the formula I can in principle also be obtained by other methods which are known per se (cf. Journal fuer Prakt. Chemie 66, p. 353; Pharm. Zentr. Halle 55, p. 735; J. Med. Chem. 20, p. 1199).

Salts are likewise obtained by common methods.

It is known that oximes can exist in two stereoisomeric forms, the syn- and antiform. Also the oxime ether of formula I according to the invention can exist in both forms and as a mixture thereof. Accordingly, within the scope of the present description are meant both stereoisomeric forms either separately or as a mixture in any reciprocal mixture ratio.

A further classification for the stereoisomeric forms is this

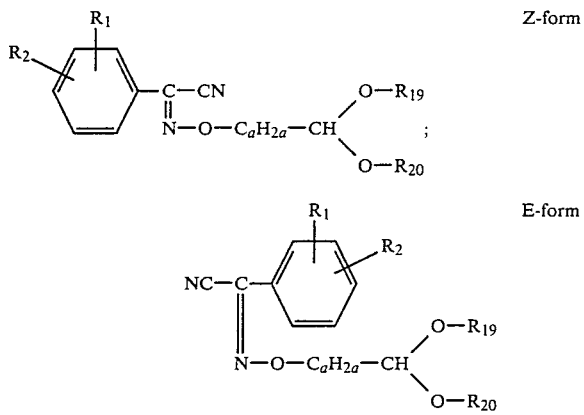

clearly distinguishing the case wherein the nitrile group is placed on the same side as the ethereal group from that wherein the nitrile group is on the opposite side. Compounds of the formula I in the Z-form (that visually corresponds to formula I above are the preferred antidotes as they tolerate plants in a wide range of application rates, even at an overdosis rate of 8 kg a.i. per hectare.

Dependingon its properties, the antidote of the formula I can be used before emergence (pre-emergence) or after emergence (post-emergence) of the plants. For example, it can be used for pretreatment of the seed of the cultivated plant (seed dressing); it can be applied into the seed furrows before sowing; it can be used for the pretreatment of cuttings; or, finally, it can be applied as a tank mixture. Furthermore, it can be employed together with the herbicide, and can be applied either by one or by several of the foregoing methods. The treatment with the antidote can be carried out before or after the herbicidal treatment, or the two treatments can be performed simultaneously. The pre-emergence treatment includes both the treatment of the cultivated area before sowing (ppi=pre plant incorporation) and the treatment of the sown cultivated area before emergence of the plants.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

The content of active substance in commercial compositions is between 0.1% and 90% by weight.

For application, the compounds of the formula I may be processed to the following formulations (in which the percentages by weight in brackets refer to advantageous amounts of active ingredient):

Solid formulations:
dusts, tracking agents (up to 10%), granules (coated granules, impregnated granules and homogeneous granules); pellets (1 to 80%);

Liquid formulations:
(a) active substance concentrates which are dispersible in water: wettable powders, pastes; (25–90% in commercial packs, 0.01 to 15% in ready for use solutions; emulsifiable concentrates and concentrated solutions (10 to 50%; 0.01 to 15% in ready for use solutions).
(b) Solutions (0.1 to 20%); aerosols.

Such compositions also constitute an object of the invention.

Surprisingly, the oxime derivative of the formula I has the property of protecting cultivated plants from attack by aggressive agrochemicals, in particular herbicides of the most diverse compound classes, including 1,3,5-triazines, 1,2,4-triazinones, phenylurea derivatives, carbamates, thiolcarbamates, phenoxyacetates, phenoxypropionates, haloacetanilides, halophenoxyacetates, substituted phenoxyphenoxyacetates and -propionates, benzoic acid derivatives, where these compounds are not tolerated or insufficiently tolerated by plants.

The rates of application of the antidote with respect to the herbicide depend largely on the mode of application. Where a field treatment is carried out, the ratio of antidote of the formula I to phytotoxic chemical is 1:100 to 5:1, preferably 1:20 to 1:1, with a corresponding amount of herbicide of approximately 0.1 to 10 kg and preferably 0.2 to 3 kg a.i. per hectare. When dressing seeds and taking similar specific protective measures, however, much lower amounts of antidote are required in comparison with e.g. the amounts of herbicide later employed per hectare of crop area (e.g. about 1:3000 to 1:1000). As a rule, protective measures such as seed dressing with an antidote of the formula I and possible later field treatment with agrochemicals are only loosely connected. Pretreated seeds and plants can later come into contact with different chemicals in agriculture, horticulture and forestry.

Accordingly, the invention relates to plant protection compositions which contain, as active ingredient, solely an antidote of the formula I together with conventional carriers. If appropriate or desired, such compositions can additionally be mixed with the chemical against the action of which it is desired to protect the cultivated plant, for example with a herbicide of the aforementioned classes, preferably a chloroacetanilide or a s-triazine.

Among the class of herbicidal s-triazines and triazinones the following known species should be especially mentioned.

2-chloro-4,6-bis(ethylamino)-s-triazine (Simazin)
2-chloro-4-ethylamino-6-isopropylamino-s-triazine (Atrazin)
2-methylthio-4,6-bis(isopropylamino)-s-triazine (Prometryn)
2-methylthio-4-ethylamino-6-tert.-butylamino-triazine (Terbutryn)
2-methylthio-4-ethylamino-6-isopropylamino-s-triazine (Ametryn)
2-chlor-4,6-bis(isopropylamino)-s-triazine
2-azido-4-methylthio-6-isopropylamino-s-triazine
2-(6 -ethylamino-4-chloro-s-triazin-2-yl-amino)-2-methylpropionitrile 2-chlor-4-cyclopropylamino-6-isopropylamino-s-triazine 4-Amino-6-tert.-butyl-3-methylthio-1,2,4-triazin-5-(4H)-one (Metribuzin)

2-methylthio-4-ethylamino-6-(1',2'-dimethyl-propylamino)-s-triazine 2-(6'-cyclopropylamino-4'-chlor-s-triazin-2'-yl-amino)-2-methyl-propionitrile 2-methylthio-4-isopropylamino-6-sec.-butylamino-s-triazine.

Cultivated plants within the scope of this invention are all plants which, in any form, can be harvested (seeds, roots, stalks, tubers, leaves, blossoms) and from which extracts can be obtained (oils, sugar, starch, protein) and which for this purpose are cultivated and tended. To these plants belong e.g. all species of cereals, maize, rice, sorghum millet such as sorghum hybridum, soybeans, beans, peas, potatoes, vegetables, cotton, sugar beet, sugar cane, ground nuts, tobacco, hops, and also ornamentals, fruit trees and bananas, cocoa and natural rubber plants. This list does not constitute a limitation.

In principle, an antidote can be employed wherever it is desired to protect a cultivated plant from the phytotoxicity of a chemical.

The invention also relates to a method of protecting cultivated plants from aggressive (phytotoxic) chemicals, which comprises applying an oxime derivative of the formula I which acts as antidote, optionally before or after application of the chemical, or also simultaneously with the chemical.

The invention also relates to the propagation products of such cultivated plants which are given a protective treatment with an oxime derivative of the formula I. By propagation products are meant all generative parts of plants which can be used for the propagation of the cultivated plant, for example grains (seeds in the narrow sense), roots, fruit, tubers, rhizomes, parts of stalks, branches (seedlings) and other parts of plants. Propagation products also include pregerminated plants and young plants which, after pregermination or emergence, will be further transplanted. Such young plants can be selectively protected by means of a complete or partial immersion treatment before transplantation.

It is the stereochemical Z-form of the oximino benzacetonitrile of the formula II which is preferably obtained by common treatment of the corresponding unsubstituted or substituted benzacetonitrile with nitrous acid or with a nitrite. Usually the E-form is retained in the solvent and can be obtained by chromatographic measures or by fractional crystallisation.

MANUFACTURING EXAMPLES

EXAMPLE 1

Manufacture of N-[2-bis(methoxy)-ethoxy]-iminobenzacetonitrile of the formula

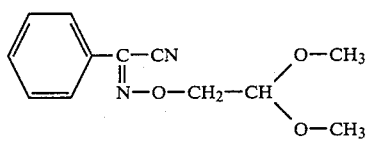

No. 1

16.9 g (0.1 mole) of bromoacetaldehyde dimethyl acetale are added to a solution of 16.8 g (0.1 mole) of the sodium salt of oximinophenylacetonitrile in 70 ml of dimethyl sulfoxide. The reaction mixture is heated for 4 hours to 60° C., cooled to room temperature, diluted with 400 ml of ether and washed with three 200 ml portions of 2% NaOH. The ethereal solution is concentrated and the crude product is recrystallized from hexane. Yield: 14 g of crystals with a melting point of 35° C.

EXAMPLE 2

Manufacture of N-(1,3-dioxolan-2-yl-methoxy)-iminobenzacetonitrile of the formula

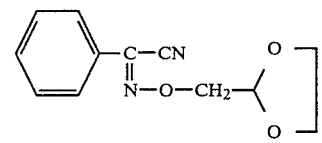

No. 2

16.7 g of 2-bromomethyldioxolan-(1.3) are dropped while stirring to a solution of 15.4 g of oximinophenylacetonitrile sodium salt (Z-form) in 70 ml of dimethyl sulfoxide. The reaction mixture is heated for 4 hours to 60° C. After cooling 300 ml of diethyl ether are added thereto and the mixture is washed with three 250 ml portions of diluted NaOH solution. The organic layer is separated off, dried over MgSO$_4$, filtered and evaporated. The oily residue crystallizes. 17.8 g are obtained, m.p. 67° C. After recrystallisation from diethyl ether/hexane (1:3) the product melts at 76°–77° C.

EXAMPLE 3

Manufacture of N-(1,3-dioxan-2-yl-methoxy)-iminobenzacetonitrile of the formula

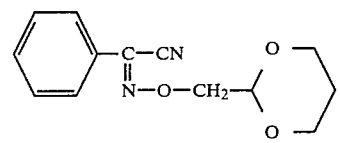

No. 3

18.1 g of 2-bromomethyl-1,3-dioxan are dropped while stirring to a solution comprising 15.4 g of oximinophenylacetonitrile sodium salt (Z-form), 0.8 g pulverized NaOH and 70 ml of dimethylsulfoxide. The reaction mixture is heated for 4.5 hours to 60° C. After cooling 300 ml of diethyl ether are added thereto and the mixture is washed with three 250 ml portions of water. The organic layer is separated off, dried over MgSO$_4$, filtered and evaporated. The oily residue crystallizes: 20.3 g end product, m.p. 42° C. After recrystallization from diisopropylether 18.2 g of the desired product are obtained, m.p. 53° C.

EXAMPLE 4

Manufacture of N-(5,5-dimethyl-1,3-dioxan-2-yl-methoxy)-imino-benzacetonitrile of the formula

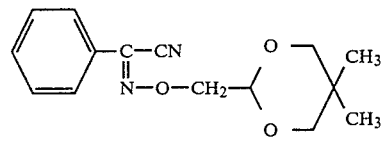

No. 4

21 g of 2-bromomethyl-5,5-dimethyl-1,3-dioxan are dropped to a mixture comprising 15 g of the sodium salt of oximinophenylacetonitrile (Z-form), 0.8 g pulverized NaOH and 70 ml of dimethyl sulfoxide. The mixture is heated to 60° C. for 4.5 hours and treated as in Example 3. The remaining oily residue crystallizes: 22 g end product, m.p. about 25° C.

In this context it should be noted that different nomenclatures may be used for the compounds of formula I herein. For example, to the compounds given hereunder a second name according to the IPUAC rules has been allotted:

No. 1 phenylacetonitrile oxime-(2',2'-dimethoxyethyl) ether = N-(2,2-dimethoxy-ethoxy)-imino-benzacetonitrile, No. 2 phenylacetonitrile oxime-(2'-ethylenedioxyethyl) ether = N-(1,3-dioxolan-2-yl-methoxy)-imino-benzacetonitrile, No. 3 phenylacetonitrile oxime-(2'-propylenedioxyethyl) ether = N-(1,3-dioxan-2-yl-methoxy)-imino-benzacetonitrile, No. 16 2-chlorophenylacetonitrile oxime-[2'-(2'',2''-dimethyl-propylenedioxy)-ethyl]ether = 2-chloro-N-(5,5-dimethyl-dioxan-2-yl-methoxy)-imino-benzacetonitrile.

The following compounds of the formula (I) can be obtained in analogous manner or by one of the methods described herein.

TABLE 1

$$Q = -C_aH_{2a}CH{\overset{OR_{19}}{\underset{OR_{20}}{<}}}$$

| Compound | $R_1$ | $R_2$ | Q | physical date (°C.) |
|---|---|---|---|---|
| 1 | H | H | $-CH_2-CH(OCH_3)_2$ | m.p. 35° |
| 2 | H | H | 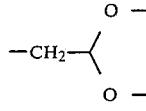 | m.p. 67° |
| 3 | H | H | 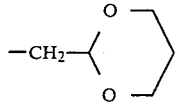 | m.p. 52–53° |
| 4 | H | H | 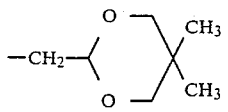 | m.p. ~30° |
| 5 | H | H | 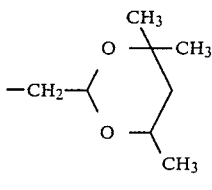 | m.p. 60° |
| 6 | H | H | $-CH_2CH(OC_2H_5)_2$ | $n_D^{21} = 1.5110$ |
| 7 | H | 4-$CH_3$ | 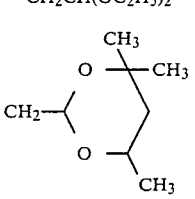 | m.p. 97° |
| 8 | H | 2-Cl | 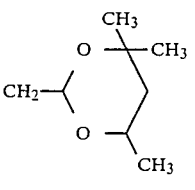 | $n_D^{24} = 1.5170$ |
| 9 | H | 4-$CH_3O$ | 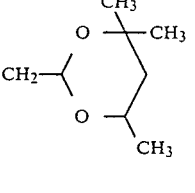 | $n_D^{24} = 1.5281$ |

TABLE 1-continued
$$Q = -C_aH_{2a}CH\begin{matrix}OR_{19}\\OR_{20}\end{matrix}$$
| Compound | $R_1$ | $R_2$ | Q | physical date (°C.) |
|---|---|---|---|---|
| 10 | H | 2-Cl | CH$_2$—CH(OCH$_3$)$_2$ | $n_D^{24}$ = 1.5304 |
| 11 | H | 4-CH$_3$ | —CH$_2$CH(OCH$_3$)$_2$ | $n_D^{24}$ = 1.5258 |
| 12 | H | 4-CH$_3$O | —CH$_2$—CH(OCH$_3$)$_2$ | $n_D^{24}$ = 1.5375 |
| 13 | 3-Cl | 4-Cl | 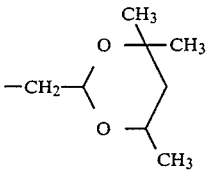 | $n_D^{24}$ = 1.5354 |
| 14 | 3-Cl | 4-Cl | —CH$_2$—CH(OCH$_3$)$_2$ | $n_D^{22}$ = 1.5523 |
| 15 | 3-Cl | 4-Cl | 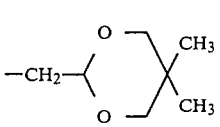 | $n_D^{22}$ = 1.5355 |
| 16 | H | 2-Cl | 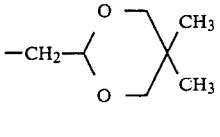 | $n_D^{22}$ = 1.5236 |
| 17 | H | 4-CH$_3$O | 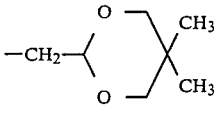 | m.p. 85° |
| 18 | H | 4-CH$_3$ | 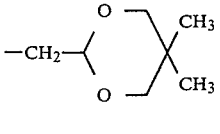 | m.p. 75° |
| 19 | H | 4-CH$_3$O | 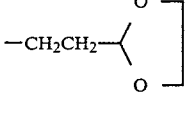 | $n_D^{21}$ = 1.5437 |
| 20 | H | 2-Cl | 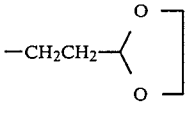 | $n_D^{24.5}$ = 1.5435 |
| 21 | 3-Cl | 4-Cl | 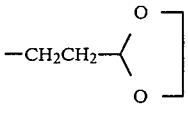 | wax |
| 22 | H | H | 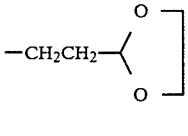 | $n_D^{24}$ = 1.5443 |
| 23 | H | 4-CN | 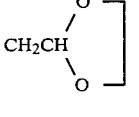 | |

TABLE 1-continued $$Q = -C_aH_{2a}CH\begin{matrix}OR_{19}\\OR_{20}\end{matrix}$$

| Compound | R$_1$ | R$_2$ | Q | physical date (°C.) |
|---|---|---|---|---|
| 24 | 2-Cl | H | $-CH_2-\underset{O}{\overset{O}{\diagdown}}\!\!\!\diagup$ (1,3-dioxolane) | m.p. 39° |
| 25 | H | 4-OCH$_3$ | CH$_2$CH(OC$_2$H$_5$)$_2$ | n$_D^{22}$ = 1.5250 |
| 26 | 2-Cl | 4-Cl | CH$_2$CH(OC$_2$H$_5$)$_2$ | n$_D^{22}$ = 1.5237 |
| 27 | H | H | C$_2$H$_4$CH(OC$_2$H$_5$)$_2$ | n$_D^{20}$ = 1.4947 |
| 28 | 2,3-C$_4$H$_4$— | | CH$_2$CH(OC$_2$H$_5$)$_2$ | n$_D^{20}$ = 1.5462 |
| 29 | 4-CH$_3$ | H | —CH$_2$—CH(1,3-dioxolane) | m.p. 55° |
| 30 | 4-OCH$_3$ | H | —CH$_2$—CH(1,3-dioxolane) | m.p. 55° |
| 31 | 4-Cl | 3-Cl | —CH$_2$—CH(1,3-dioxolane) | m.p. 65° |
| 32 | 4-CH$_3$ | H | —CH$_2$—CH(1,3-dioxane) | m.p. 59° |
| 33 | 4-OCH$_3$ | H | —CH$_2$—CH(1,3-dioxane) | m.p. 59° |
| 34 | 2-Cl | H | —CH$_2$—CH(1,3-dioxane) | |
| 35 | 4-Cl | 3-Cl | —CH$_2$—CH(1,3-dioxane) | |
| 36 | 4-OCH$_3$ | H | —CH$_2$—CH$_2$—CH(1,3-dioxolane) | n$_D^{24}$ = 1.5492 |
| 37 | H | H | —CH$_2$—CH$_2$—CH(1,3-dioxolane) | n$_D^{23.5}$ = 1.5420 |
| 38 | 4-CH$_3$ | H | —CH$_2$—CH(OC$_2$H$_5$)$_2$ | n$_D^{21.5}$ = 1.5149 |
| 39 | 4-Cl | 3-Cl | —CH$_2$—CH(OC$_2$H$_5$)$_2$ | n$_D^{22}$ = 1.5303 |
| 40 | 4-Cl | H | —CH$_2$—CH(OC$_2$H$_5$)$_2$ | n$_D^{20}$ = 1.5190 |
| 41 | 4-CH$_3$ | H | —CH$_2$—CH$_2$—CH(OC$_2$H$_5$)$_2$ | n$_D^{24}$ = 1.5008 |
| 42 | 4-OCH$_3$ | H | —CH$_2$—CH$_2$—CH(OC$_2$H$_5$)$_2$ | n$_D^{24}$ = 1.5114 |
| 43 | 4-Cl | 3-Cl | —CH$_2$—CH$_2$—CH(OC$_2$H$_5$)$_2$ | n$_D^{24}$ = 1.5220 |
| 44 | 4-Cl | 2-Cl | —CH$_2$—CH$_2$—CH(OC$_2$H$_5$)$_2$ | n$_D^{24}$ = 1.5143 |
| 45 | 4-Cl | H | —CH$_2$—CH$_2$—CH(OC$_2$H$_5$)$_2$ | n$_D^{24}$ = 1.5103 |
| 46 | 2,3-C$_4$H$_4$— | | —CH$_2$—CH$_2$—CH(OC$_2$H$_5$)$_2$ | n$_D^{24}$ = 1.5400 |

TABLE 1-continued $$Q = -C_aH_{2a}CH\begin{matrix}OR_{19}\\OR_{20}\end{matrix}$$

| Compound | R₁ | R₂ | Q | physical date (°C.) |
|---|---|---|---|---|
| 47 | 4-Cl | 2-Cl | —CH₂—CH(OCH₂CH₂O) (cyclic) | $n_D^{24} = 1.5475$ |
| 48 | 4-Cl | H | —CH₂—CH(OCH₂CH₂O) (cyclic) | $n_D^{24} = 1.5493$ |
| 49 | 2,3-C₄H₄— | | —CH₂—CH(OCH₂CH₂O) (cyclic) | $n_D^{24} = 1.5842$ |
| 50 | 4-Cl | 2-Cl | —CH₂—CH(OCH₃)₂ | $n_D^{24} = 1.5428$ |
| 51 | 2,3-C₄H₄— | | —CH₂—CH(OCH₃)₂ | $n_D^{24} = 1.5707$ |
| 52 | 4-Cl | 2-Cl | —CH₂—CH(OCH₂C(CH₃)₂CH₂O) (cyclic) | $n_D^{24} = 1.5377$ |
| 53 | H | H | —CH₂—CH(OCH₂C(Et)₂CH₂O) (cyclic) | $n_D^{22} = 1.5266$ |
| 54 | 4-CH₃ | H | —CH₂—CH(OCH₂C(Et)₂CH₂O) (cyclic) | m.p. 118–120° |
| 55 | 4-Cl | 3-Cl | —CH₂—CH(OCH₂C(Et)₂CH₂O) (cyclic) | m.p. 88–95° |
| 56 | 3-CF₃ | H | —CH₂CH(OCH₃)₂ | |
| 57 | 3-CF₃ | H | —CH₂CH(OC₂H₅)₂ | |
| 58 | 3-CF₃ | H | —CH₂CH(OCH₂CH₂O) (cyclic) | |
| 59 | 3-CF₃ | H | —CH₂CH(OCH₂CH₂CH₂O) (cyclic) | |
| 60 | 3-CF₃ | H | —CH₂CH(OCH₂C(CH₃)₂CH₂O) (cyclic) | |
| 61 | 3-Cl | H | —CH₂CH(OCH₃)₂ | |
| 62 | 3-Cl | H | —CH₂CH(OC₂H₅)₂ | |

TABLE 1-continued $$Q = -C_aH_{2a}CH\begin{matrix}OR_{19}\\OR_{20}\end{matrix}$$

| Compound | R₁ | R₂ | Q | physical date (°C.) |
|---|---|---|---|---|
| 63 | 3-Cl | H | 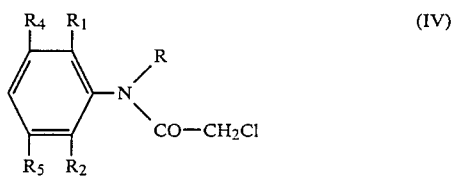 | |
| 64 | 3-CH₃ | H | —CH₂CH(O—CH₂—O) (1,3-dioxolane) | |
| 65 | 3-OCH₃ | H | —CH₂CH(OCH₃)₂ | |
| 66 | 3-CH₃ | H | —CH(OC₂H₅)₂ | |
| 67 | 3-OCH₃ | H | —CH₂CH(O—CH₂—O) | |

The antidote compound of formula I is particularly effective as safening agent for chloroacetanilide herbicides. Chloroacetanilides usable as highly effective active substances which on their own damage cultivated plants, such as cereals, rice, sorghum hyb. and cultivated millet varieties, but which when used together with the oxime ether according to the invention no longer appreciable attach these cultivated plants whilst retaining the herbicidal effectiveness against weeds, have become known, for example, U.S. Pat. Nos. 3,547,620; 3,403,994; 3,442,945; 3,637,847; 3,598,859; 3,819,661; 3,937,730; 3,946,045; 3,983,174; also from German Offenlegungsschrift Nos. 2,212,268; 2,305,495; 2,402,983; 2,405,183 and 2,405,479.

The antidote according to the invention is preferably used to protect cultural plants from the phototoxicity of herbicidal chloroacetanilides which correspond to the formula IV $$\begin{matrix}R_4 & R_1 \\ & \\ R_5 & R_2\end{matrix}\text{-phenyl-N(R)-CO-CH}_2\text{Cl} \quad (IV)$$

wherein $R_1$ is a lower alkyl, alkoxy, alkoxyalkyl or trifluoromethyl group or a halogen atom, and $R_2$, $R_4$ and $R_5$ independently of one another are hydrogen, a lower alkyl, alkoxy, alkoxyalkyl or trifluoromethyl group or a halogen atom, and R is an alkyl group having 1 to 4 carbon atoms which may be substituted by carboxy, carboxylic acid ester, carboxylic acid amide, carboxylic acid (mono- or di-lower aliphatic) amide or a cyano group; or wherein R is a propinyl, a butinyl, an acetalized carbonylalkyl, a 1,3-dioxolan-2-yl-alkyl, a 1,3-dioxolan-5-yl-alkyl, a 1,3-dioxan-2-yl-alkyl, a furanylmethyl, a tetrahydrofuranylmethyl group or an alkoxyalkyl group of the form —A—O—R₃, in which A is an alkylene group having 1 to 4 carbon atoms of which 1 or 2 are in the direct chain, and $R_3$ is a lower alkyl or alkenyl group or a cycloalkyl or cycloalkylmethyl group having 3 to 6 ring carbon atoms.

As used herein, the term "lower" as applied to alkyl groups and other hydrocarbon groups refers to groups having up to four carbon atoms. These include, in the case of lower alkyl, methyl, ethyl, n-propyl, isopropyl, n-butyl, isobutyl, sec.butyl and tert.butyl. By "halogen" is meant fluorine, chlorine, bromine and iodine, particularly fluorine and chlorine.

One of the groups of herbicidal chloroacetanilides preferably used are those where in the above formula IV $R_1$ is hydrogen or alkyl having 1 to 4 carbon atoms, $R_2$ is alkyl having 1 to 4 carbon atoms, R is alkyl having 1 to 4 carbon atoms which is substituted by a carboxylic acid ester group, or an alkoxyalkyl group of the formula —A—O—R₃, wherein A is an alkylene group having 2 or 3 carbon atoms of which 1 or 2 are in the direct chain, $R_3$ is alkyl having 1 to 4 carbon atoms or alkenyl having 2 to 4 carbon atoms, and $R_4$ and $R_5$ are hydrogen.

Some herbicidal chloroacetanilides which can be used are listed below:

N-ethoxymethyl-2-methyl-6-ethyl-chloroacetanilide, (acetochlor),

N-methoxymethyl-2,6-diethyl-chloroacetanilide, (alachlor),

N-(2'-methoxyethyl)-2,6-dimethyl-chloroacetanilide,

N-(2'-allyloxyethyl)-2,6-dimethyl-chloroacetanilide,

N-(2'-n-propoxyethyl)-2,6-dimethyl-chloroacetanilide,

N-(2'-isopropoxyethyl)-2,6-dimethyl-chloroacetanilide,

N-(2'-methoxyethyl)-2-methyl-6-ethyl-chloroacetanilide,

N-(2'-methoxyethyl)-2,6-diethyl-chloroacetanilide,

N-(2'-ethoxyethyl)-2-methyl-6-ethyl-chloroacetanilide,

N-(1'-ethoxycarbonyl-ethyl)-2,6-dimethyl-chloroacetanilide,

N-[3'-methoxyprop-(2')-yl]-2-methyl-chloroacetanilide,

N-[3'-methoxyprop-(2')-yl]-2,6-dimethyl-chloroacetanilide,

N-[3'-methoxyprop-(2')-yl]-2-methyl-6-ethyl-chloroacetanilide, (metolachlor),
N-[3'-methoxyprop-(2')-yl]-2,6-diethyl-chloroacetanilide,
N-[3'-methoxyprop-(2')-yl]-2-ethyl-chloroacetanilide,
N-(2'-ethoxyethyl)-2,6-diethyl-chloroacetanilide,
N-(2'-n-propoxyethyl)-2-methyl-6-ethyl-chloroacetanilide,
N-(2'-n-propoxyethyl)-2,6-diethyl-chloroacetanilide, (pretilachlor),
N-(2'-isopropoxyethyl)-2-methyl-6-ethyl-chloroacetanilide,
N-chloroacetyl-2,6-dimethylanilino-acetic acid ethyl ester,
N-chloroacetyl-2,6-diethylanilino-acetic acid ethyl ester,
N-chloroacetyl-2,6-dimethylanilino-acetic acid methyl ester,
N-chloroacetyl-2-methyl-6-ethylanilino-acetic acid isopropyl ester,
β-(N-chloroacetyl)-2,6-dimethylanilino)-propionic acid methyl ester,
α-(N-chloroacetyl-2-methyl-6-ethylanilino)-propionic acid ethyl ester,
2-[N-(α-chloroacetyl)-2,6-dimethylanilino]acetaldehyde-diethylacetale,
N-[3'-methoxyprop-(2')-yl]-2,3-dimethyl-chloroacetanilide,
N-(2'-ethoxyethyl)-2-methyl-chloroacetanilide,
N-(2'-methoxyethyl)-2-methyl-chloroacetanilide,
N-[2'-methoxyprop-(1')-yl]-2,6-dimethyl-chloroacetanilide,
N-[2'methoxyprop-(1')-yl]-2-methyl-6-ethyl-chloroacetanilide,
N-[3'-ethoxyprop-(2')-yl]-2-methyl-6-ethyl-chloroacetanilide,
N-(2'-ethoxyethyl)-2-fluoro-chloroacetanilide,
N-[3'-ethoxyprop-(2')-yl]-2-fluoro-chloroacetanilide,
N-[1'-methoxybut-(2')-yl]-2,6-dimethyl-chloroacetanilide,
N-(2'-methoxyethyl)-2-methyl-6-methoxy-chloroacetanilide,
N-(n-butoxymethyl)-2-tert.butyl-chloroacetanilide,
N-[3'-ethoxyprop-(2')-yl]-2,6-dimethyl-chloroacetanilide,
N-(2'-methoxyethyl)-2-chloro-6-methyl-chloroacetanilide,
N-(2'-ethoxyethyl)-2-chloro-6-methyl-chloroacetanilide,
N-(2'-ethoxyethyl)-2,3,6-trimethyl-chloroacetanilide,
N-(2'-methoxyethyl)-2,3,6-trimethyl-chloroacetanilide,
N-(2'-isopropoxyethyl)-2,3,6-trimethyl-chloroacetanilide,
N-cyanomethyl-2,6-dimethyl-chloroacetanilide,
N-(but-1-yn-3-yl)-chloroacetanilide,
N-propynyl-2-methyl-6-ethyl-chloroacetanilide,
N-(1,3-dioxolan-2-ylmethyl)-2,6-dimethyl-chloroacetanilide,
N-(1,3-dioxolan-2-ylmethyl)-2-ethyl-6-methyl-chloroacetanilide,
N-(1,3-dioxan-2-ylmethyl)-2-methyl-6-ethyl-chloroacetanilide,
N-(2'-furanyl-methyl)-2,6-dimethyl-chloroacetanilide,
N-(2'-furanyl-methyl)-2-chloro-6-methyl-chloroacetanilide,
N-(2'-tetrahydrofuranyl-methyl)-2,6-dimethyl-chloroacetanilide,
N-(N'-propargylcarbamylmethyl)-2,6-dimethyl-chloroacetanilide,
N-(N',N'-dimethylcarbamylmethyl)-2,6-dimethyl-chloroacetanilide,
N-(n-butoxymethyl)-2,6-diethyl-chloroacetanilide, (butachlor),
N-(2'-n-butoxyethyl)-2,6-diethyl-chloroacetanilide,
N-[3'-methoxybut-(2')-yl]-2,6-dimethylchloroacetanilide,
N-isopropyl-chloroacetanilide, (propachlor).

Many of the herbicidal chloroacetanilides mentioned above and other herbicidal chloroacetanilides of this type and the production thereof have been described in the aforementioned U.S. patents and German Offenlegungsschriften.

Particularly suitable chloroacetanilides for use in this invention are acetochlor, alachlor, metolachlor, pretilachlor, butachlor, propachlor, N-[3'-methoxyprop-(2')-yl]-2,6-dimethyl-chloroacetanilide.

The antidotes of this invention may also be used with herbicidal compositions comprising the above described chloroacetanilides and other herbicidal compounds, e.g. triazine herbicides described in, e.g., U.S. Pat. Nos. 2,891,855 and 2,909,420.

The applied amount of the antidote varies between about 0.01 and about 15 parts by weight per part by weight of halogenoacetanilide, thiolcarbamate, 1,3,5-triazine or other herbicide. The most suitable ratio with regard to the optimum action in the case of the specific cultivated plant is determined from case to case, i.e. depending on the employed chloroacetanilide, thiolcarbamate or other herbicide.

As mentioned initially, various methods and techniques can be employed for the use of the novel antidote of formula I together with herbicidal active substances or mixtures of active substances of the chloroacetanilide class, of the triazine class or of the thiolcarbamate class.

1. Seed dressing a. Dressing of the seed with an antidote formulated as an emulsion concentrate by shaking of the constituents in a vessel until there exists a uniform distribution over the surface of the seeds (wet dressing). The amount of antidote used for this purpose is about 10 to 500 g (40 g to 2 kg of wettable powder) per 100 kg of seed.

b. Dressing by immersion of the seed in a liquor containing 50–3200 ppm of antidote for 1–20 hours and subsequent drying of the seed (immersion dressing).

2. Application as tank mixture.

A liquid preparation of a mixture of antidote and herbicide (quantitative ratio between 10:1 and 1:10) is used, with the applied amount of herbicide being 0.1 to 10 kg per hectare. This tank mixture is preferably applied before emergence (either before or after sowing), or it is worked into the unsown soil to a depth of 5–10 cm.

3. Application into the seed furrow.

The antidote is introduced, as an emulsion concentrate, wettable powder or granulate, into the open sown seed furrow and, after the covering of the seed furrow in the normal manner, the herbicide is applied either before or after emergence of the plants.

The antidote can therefore be applied before, together with, or after the herbicide, and its application to the seeds or to the field before emergence can be effected either before or after sowing; or in certain cases it can be effected also after germination of the seed (post-emergence).

If the antidote is applied simultaneously with the herbicide, this is accomplished by the use of a preparation according to the invention, which preparation contains the oxime ether of formula I and at least one herbicide from the chloroacetanilide, triazine or any other class, together with additives such as carriers and/or distribution agents.

The process according to the invention for the selective control of weeds in cultivated crops, especially of the sorghum and rice genera, is such that the seeds of the cultivated plants or the cultivated areas intended for sowing or already sown, or on which the sown plants have already emerged, are treated, simultaneously, or successively in any desired sequence and at a suitable interval of time, on the one hand with a compound of formula I as the antidote protecting the cultivated plants or the seed thereof, and on the other hand with at least one herbicidal active substance, preferably of the chloroacetanilide class.

The compositions used, which contain herbicide and antidote separately or together, can be in any suitable conventional form. They can be produced in a manner known per se by the intimate mixing and grinding of the active substance(s) (including antidote) with suitable carriers and/or distributing agents, optionally with the addition of dispersing agents or solvents.

The usual forms of such compositions are either solid, such as dusts, scattering agents and granulates; or liquid, such as solutions and aqueous dispersions; or they are water-dispersible concentrates of active substance, such as wettable powders, emulsion concentrates or pastes.

In addition to the safener action of the antidote of formula I according to the invention, there is observed a certain antagonising counteraction moreover on the growth-inhibiting effect of some growth regulators on grasses in the case of overdosage of the growth inhibitor. Furthermore, the compound of formula I, used on its own, exhibits a germination-stimulating action on certain seed varieties, such as those of sorghum, rice, soybeans with increased yield at harvest time.

FORMULATION EXAMPLES

Example A

Dusts: The following substances are used to formulate (a) 5% and (b) a 2% dust:

(a)

5 parts of active substance No. 2
95 parts of talc;

(b)

2 parts of active substance No. 16
1 part of highly dispersed silicic acid
97 parts of talc.

The active substances are mixed with the carriers and ground and in this form can be processed to dusts for application.

Example B

Granulate: The following substances are used to formulate a 5% granulate:
  5 parts of active substance No. 2
  0.25 part of epoxidized vegetable oil
  0.25 part of cetyl polyglycol ether
  3.25 parts of polyethylene glycol
  91 parts of kaolin (paricle size 0.3–0.8 mm).

The active substance is mixed with epoxidized vegetable oil and the mixture is dissolved in 6 parts of acetone. Then polyethylene glycol and cetyl polyglycol ether are added. The resultant solution is sprayed on kaolin and the acetone is evaporated in vacuo.

Example C

Wettable powders: The following constituents are used to formulate (a) a 70%, (b) a 40%, (c) and (d) a 25% and (e) a 10% wettable powder:

(a)

70 parts of active substance No. 2
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk (b)

40 parts of active substance No. 1
5 parts of sodium ligninsulfonate
1 part of sodium dibutylnaphthalenesulfonic acid
54 parts of silicic acid (c)

25 parts of active substance No. 2
4.5 parts of calcium ligninsulfate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)

25 parts of active substance No. 4
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)

10 parts of active substance No. 2
3 parts of a mixture of the sodium salts of saturated fatty alcohol sulfates
5 parts of naphthalenesulfonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants, such as seed or other propagation material.

Example D

Emulsifiable concentrate: The following substances are used to formulate a 25% emulsifiable concentrate:
  25 parts of active substance No. 2
  2.5 parts of epoxidized vegetable oil
  10 parts of an alkylarysulfonate/fatty alcohol polyglycol ether mixture 5 parts of dimethyl formamide 57.5 parts of xylene.

By diluting such a concentrate with water it is possible to prepare emulsions of the desired concentration, which are especially suitable for leaf or seed application.

The following tests were carried out to determine the selective action of herbicides of various chemical classes on its own or together with an antidote of formula I according to the invention; N-[3'-methoxypropyl-(2')]-2-methyl-6-ethyl-chloroacetanilide (U.S. Pat. No. 3,937,730) (metolachlor) of the formula

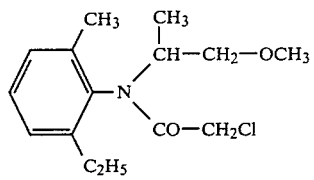

is one of the preferred herbicides.

BIOLOGICAL EXAMPLES

Example 1

Pre-emergence antidote test (basic test)

General test method: Small flower pots (diameter 6 cm at the top) are filled with garden soil into which the plant seed is sown, covered with the soil and gently pressed firm. Then the antidote is sprayed as test substance in the form of a dilute solution (obtained from a wettable powder) in an amount corresponding to 4 kg/ha. The herbicide is sprayed onto the soil directly afterwards in corresponding amount. After the pots have stood for 18 days at about 20°–23° C. and 60–70% relative humidity, evaluation is made in accordance with linear scale from 1 (denoting total damage to the plant) to 9 (denoting undamaged healthy plant). Plants without antidote protection are used as control.

The following herbicides and plants were employed:
(1) 1.5 kg/ha of α-[4-(p-trifluoromethylphenoxy)-phenoxy]-propionic acid n-butoxyethyl ester in maize of the "Orla 264" variety.
(2) 1.5 kg/ha of Metolachlor=N-[3'-methoxyprop-(2')-yl]-2-methyl-6-ethylchloroacetanilide in sorghum of the "Funk G-522" variety.
(3) 2 kg/ha of Prometryn=2,4-bis(isopropylamino)-6-methylthio-s-triazine in soybeans.
(4) 2 kg/ha of 4-ethylamino-6-tert.butylamino-2-chloro-s-triazine in wheat of the "Farnese" variety.
(5) 4 kg/ha of Prometryn=2,4-bis(isopropylamino)-6-methylthio-s-triazine in sorghum of the "Funk G-522" variety.
(6) 2 kg/ha of α-[4-(p-trifluoromethylphenoxy)-phenoxy]-propionic acid n-butoxyethyl ester in barley of the "Mazurka" variety.

A good antidote action is obtained in these tests with the compounds of the formula I. The results are e.g. as follows:

| Test variant | Compound | Rating of the herbicidal action (without/with antidote) |
|---|---|---|
| 5 | 3 | 4/7 |
| 5 | 4 | 4/6 |
| 5 | 5 | 4/7 |
| 6 | 2 | 3/7 |

| Test variant | Compound | Rating of the herbicidal action (without/with antidote) |
|---|---|---|
| 6 | 24 | 5/7 |

The results were evaluated according to the following linear ratings:
9=plants undamaged (as in the case of the untreated control plants),
1=plants completely destroyed,
2–8=intermediate stages of damage.

Example 2

Antidote action on separate application (antidote/pre-emergence, herbicide/post-emergence)

General test method:

Small flower pots (diameter 6 cm at the top) are filled with sandy loam into which the plant is sown. After covering the seed, a dilute solution of the antidote as test substance is sprayed onto the surface of the soil in an amount corresponding to 4 kg/ha. The pots are kept at 20°–23° C. and 60–70% relative humidity. When the plants have attained the 2- to 3-leaf stage after 10 days, they are treated as indicated below with the corresponding amount of herbicide. Evaluation is made 14 days after the application of the herbicide, using the same rating system as in Example 1. Plants unprotected by antidote are used as control.

The herbicides and plants employed are:
(1) 4 kg/ha of Ametryn=2-ethylamino-4-isopropylamino-6-methylthio-s-triazine in maize of the "Orla 264" variety.
(2) 1 kg/ha of Prometryn=2,4-bis(isopropylamino)-6-methylthio-s-triazine in sorghum of the "Funk G-522" variety.
(3) 0.25 kg/ha of α-[4-(p-trifluoromethylphenoxy)-phenoxy]-propionic acid n-butoxyethyl ester in barley of the "Mazurka" variety.

A good antidote action was obtained in these tests with compounds of the formula (I).

Example 3

Antidote action in transplanted rice on separate application (antidote/pre-emergence, herbicide/post-emergence)

Plastic tubs measuring 8×8×10 cm are filled with wet marshy soil to 2 cm below the edge. A dilute solution of the antidote as test substance is sprayed onto the surface of the soil in an amount corresponding to 4 kg/ha. Rice plants of the "IR-8" variety are transplanted in the 1½- to 2-leaf stage into the prepared tubs. On the next day, the water level is raised to about 1.5 cm. Four days after transplantation, 2-ethylamino-4-(1,2-dimethyl-n-propylamino)-6-methylthio-s-triazine is added to the water in granule form in an amount corresponding to 0.75 kg/ha. During the test, the temperature is 26°–28° C. and the relative humidity 60–80%. Evaluation is made 20 days after the treatment with herbicide, using the same rating as in Example 1. Plants not protected with antidote are used as control. A good antidote action is obtained in this test with compounds of the formula I.

| Compound | Rating of the herbicidal action (without/with antidote) |
|---|---|
| 2 | 2/4 |

-continued

| Compound | Rating of the herbicidal action (without/with antidote) |
| --- | --- |
| 1 | 2/6 |
| 3 | 4/7 |
| 4 | 4/8 |
| 19 | 5/7 |
| 21 | 3/6 |

Example 4

Pre-emergence antidote test in nutrient solution

A Hewitt nutrient solution, which contains the amount of herbicide indicated below as well as 10 ppm of the antidote to be tested, is prepared.

Seeds which would normally be damaged in the indicated test concentrations of the herbicide employed are sown in granular zonolith (expanded vermiculite) in plastic flower pots (diameter 6 cm at the top) which are perforated at the bottom. Each pot is then placed in a second transparent plastic flower pot (diameter 7 cm at the top) which contains about 50 ml of the nutrient solution prepared with herbicide and antidote. This nutrient solution then rises by capillary action in the filling material of the smaller pot and moistens the seed and the germinating plant. The loss in fluid is daily replenished to 50 ml with pure Hewitt nutrient solution. Evaluation is made 3 weeks after the start of the test, using the same rating as in Example 1. The control solution employed in the parallel test contains no antidote.

The herbicides and plants employed are:
(1) 4 ppm of Prometryn=2,4-bis(isopropylamino)-6-methylthio-s-triazine in sorghum of the "Funk G-522" variety.
(2) 4 ppm of 4-ethylamino-6-tert.butylamino-2-chloro-s-triazine in wheat of the "Farnese" variety.
(3) 4 ppm of α-[4-(p-trifluoromethylphenoxy)-phenoxy]-propionic acid n-butoxyethyl ester in barley of the "Mazurka" variety.
(4) 5 ppm of Metolachlor=N-[3'-methoxyprop-(2')-yl]-2-methyl-6-ethylchloroacetanilide in sorghum of the "Funk G-522" variety.

A good antidote action is obtained with the compounds of the formula I. The results are e.g. as follows:

| Test variant | Compound | Rating of the herbicidal action without/with antidote |
| --- | --- | --- |
| 1 | 15 | 3/6 |
| 4 | 1 | 4/7 |
| 4 | 2 | 4/7 |
| 4 | 3 | 4/7 |
| 4 | 4 | 4/7 |
| 4 | 14 | 3/7 |
| 4 | 15 | 3/8 |
| 4 | 16 | 3/8 |

Example 5

Pre-emergence antidote test in nutrient solution (rice)

A Hewitt nutrient solution, which additionally contains 10 ppm of the antidote to be tested, is prepared.

Rice seeds of the "IR-8" variety are sown in granular filling material (granular zonolith) in plastic flower pots (diameter 6 cm at the top) which are perforated at the bottom. Each pot is then placed in a second transparent plastic flower pot (diameter 7 cm at the top) which contains about 50 ml of the nutrient solution prepared from herbicide and antidote. This nutrient solution then rises by capillary action in the filling material of the smaller pot and moistens seed and plant. The loss in fluid is daily replenished to 50 ml with pure Hewitt solution. After 15 days, the rice plants are transplanted in the 2- to 2½-leaf stage in rectangular plastic pots (8×8×10 cm) which are filled with 500 ml of wet, marshy soil. The water level is increased next day to 1–2 cm above the level of the soil. Four days after transplantation, the herbicide 2-ethylamino-4-(1,2-dimethyl-n-propylamino)-6-methylthio-s-triazine is added in granule form in an amount corresponding to 0.75 kg/ha. Evaluation is made 3 weeks later in accordance with the rating employed in Example 1 and subsequent Examples. The control solution used in the parallel test contains no antidote. A good antidote action was obtained in this test with the compound of the formula (I). The results are e.g. as follows:

| Compound | Herbicidal action without/with antidote |
| --- | --- |
| 26 | 2/6 |
| 25 | 5/6 |

Example 6

Post-emergence antidote test in nutrient solution
General test method:

Small plastic flower pots (diameter 6 cm at the top), which are perforated at the bottom, are filled with granular zonolith and the seeds are sown in this material. Each pot is then placed in a second transparent plastic flower pot (diameter 7 cm at the top) which contains 50 ml of water which rises by capillar action and moistens the seed. From the 5th day, the continual loss in water is made up with Hewitt nutrient solution. From the 15th day, when the plant is in the 1½-2-leaf stage, 10 ppm of the antidote to be tested and the amount of herbicide indicated below are added to the nutrient solution which has again been replenished to 50 ml. From the 16th day, the loss in fluid is again made with pure Hewitt nutrient solution. During the entire duration of the test, the temperature is 20°–23° C. and the relative humidity 60–70%. Evaluation is made 3 weeks after the addition of the herbicide in accordance with the rating employed in Example 1 and subsequent Examples:

Test variants:
(1) 15 ppm of α-[4-(3,5-dichloropyridyl-2-oxy)-phenoxy]-propionic acid propargylthiolo-ester in wheat of the "Zenith" variety.
(2) 4 ppm of 4-ethylamino-6-tert.butylamino-2-chloro-s-triazine in wheat of the "Zenith" variety.
(3) 2 ppm of α-[4-(p-trifluoromethylphenoxy)-phenoxy]-propionic acid n-butoxyethyl ester in maize of the "Orla" variety.
(4) 8 ppm of α-[4-(p-trifluoromethylphenoxy)-phenoxy]-propionic acid n-butoxyethyl ester in sorghum of the "Funk G-522" variety.
(5) 4 ppm of Prometryn=2,4-bis(isopropylamino)-6-methylthio-s-triazine in sorghum of the "Funk G-522" variety.
(6) 8 ppm of α-[4-(3,5-dichloropyridyl-2-oxy)-phenoxy]-propionic acid methyl ester in wheat of the "Zenith" variety.

A good antidote action is obtained in these tests with compounds of the formula (I).

Example 7

Antidote test-seed soaking

Rice seeds of the "IR-8" variety are immersed for 48 hours in solutions of the test substances in concentrations of 10, 100 or 1000 ppm. The seeds are then allowed to dry for about 2 hours until they are no longer tacky. Rectangular plastic tubs (8×8×10 cm) are filled with sandy loam to 2 cm below the edge. 4 g of seeds are sown in each tub and only very loosely covered (to about the diameter of the seed). The soil is kept in a moist (non-marshy) state. Then a dilute solution of the herbicide Metolachlor is applied in an amount corresponding to 2.0, 1.0 and 0.5 kg herbicide per hectare. The pots were stored at 20°–22° C. during the night and 28°–30° C. during the day with the required amount of watering. By means of artificial lighting, the length of the day and the night was adjusted to 12 hours each.

The evaluation was carried out after 21 days according to the ratings of Example 1. The values are given in the following Table 2, and apply to both the Sorghum varieties used in this test. It is noticeable how the strong herbicidal action of common chloroacetanilides on Sorghum cultures is reduced or completely eliminated in the presence of an antidote of the formula I.

TABLE 2

Antidote activity of compound No. 2 in Sorghum in the presence of chloroacetanilides

| | amounts of herbicide | | | | | | | | | | | | | | |
|---|---|---|---|---|---|---|---|---|---|---|---|---|---|---|---|
| | 2.0 kg herbicide/hectare | | | | | 1.0 kg herbicide/hectare | | | | | 0.5 kg herbicide/hectare | | | | |
| | amounts of antidote (safener) | | | | | | | | | | | | | | |
| g a.i./kg seed | none | 4.0 | 2.0 | 1.0 | 0.5 | none | 4.0 | 2.0 | 1.0 | 0.5 | none | 4.0 | 2.0 | 1.0 | 5.0 |
| i (metolachlor) | 2 | 6 | 6 | 8 | 5 | 2 | 7 | 8 | 8 | 7 | 4 | 7 | 8 | 8 | 8 |
| ii (alachlor) | 2 | 7 | 8 | 8 | 7 | 2 | 8 | 8 | 8 | 8 | 3 | 8 | 8 | 8 | 8 |
| iii | 2 | 6 | 6 | 5 | 5 | 2 | 7 | 5 | 6 | 4 | 3 | 8 | 8 | 8 | 7 |
| iv (acetochlor) | 1 | 5 | 7 | 4 | 4 | 2 | 7 | 6 | 6 | 6 | 2 | 7 | 7 | 7 | 7 | i = metolachlor = N—[3'-methoxyprop-(2')-yl]-2-methyl-6-ethyl-chloroacetanilide
ii = alachlor = N—methoxymethyl-2,6-diethyl-chloroacetanilide
iii = N—[3'-methoxyprop-(2')-yl]-2,6-dimethyl-chloroacetanilide
iv = acetochlor = N—ethoxymethyl-2-methyl-6-ethyl-chloroacetanilide sponding to 1.5 kg/ha. Evaluation is made 7 and 18 days after transplantation in accordance with the rating employed in Example 1 and subsequent Examples. A good antidote action is obtained in this test with compounds of the formula (I), in particular with compounds 1, 2 and 11.

Example 8

Antidote test (root dipping)

Rice plants of the "IR-8" variety are reared in soil until they are in the 1½- to 2-leaf stage and then superficially washed. Then only the roots of the plants, in bunches, are dipped for 45 minutes in a dish containing solutions of the test substance in a concentration of 10, 100 or 1000 ppm. The plants are then transplanted in sandy loam in containers measuring 47×29×24 cm. The surface of the soil is covered with water to a height of 1½ to 2 cm. One day after transplantation, a dilute solution of the herbicide N-(2'-n-propoxyethyl)-2,6-diethylchloroacetanilide, is pipetted directly into the water in an amount corresponding to 1.5 kg/ha. Evaluation is made 7 and 18 days after transplantation in accordance with the rating employed in Example 1 and subsequent Examples. Good antidote action is obtained in this test with compounds of the formula (I).

Example 9

Antidote test (seed treatment)

(a) Seed dressing (wet)

Aqueous emulsion concentrates of the antidote No. 2 [=N-(1,3-dioxolan-2-yl-methoxy)imino-benzacetonitrile] were prepared, and 50 g of the cultivated millet seed Sorghum hybridum (Variety "Funk G-522" and variety "Dekalb") in a bottle were treated with one liter of said formulation by shaking. The concentrates used were made up to correspond to 4 g, 2 g, 1 g and 0.5 g a.i. per kg seed.

(b) Antidote activity

Shortly after the dressing, the seed was sown in loamy soil in pots. The soil was treated immediately with 0.4% aqueous liquors containing a chloroacetanilide herbicide in amounts corresponding to 2.0, 1.0 and 0.5 kg herbicide per hectare.

I claim:

1. A composition for protecting sorghum, rice and barley crops gainst the action of 1,3,5-triazine, haloacetanilide or phenoxyphenoxypropionate herbicides which comprises (1) a crop protecting effective amount of a compound of the formula

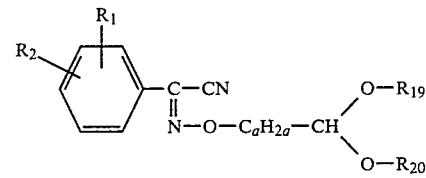

wherein,
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl, or ethyl
$R_{19}$ and $R_{20}$ taken together is $C_2$–$C_7$ alkylene having 2 or 3 carbon atoms in its principal chain and (2) a carrier.

2. A composition according to claim 1 wherein in the formula $R_1$ is hydrogen and $R_2$ is hydrogen or chlorine.

3. A composition according to claim 2 wherein the crop protecting compound is phenylacetonitrile oxime-(2',2'-dimethoxyethyl) ether.

4. A composition according to claim 2 wherein the crop protecting compound is phenylacetonitrile oxime-(2'-ethylenedioxyethyl) ether.

5. A composition according to claim 2 wherein the crop protecting compound is phenylacetonitrile oxime-(2'-propylenedioxyethyl) ether.

6. A composition according to claim 2 wherein the crop protecting compound is 2-chlorophenylacetonitrile oxime-[2'-(2'',2''-dimethyl-propylenedioxy)-ethyl]ether.

7. A herbicidal composition comprising (1) a 1,3,5-triazine, haloacetanilide or phenoxyphenoxypropionate herbicide and (2) compound of the formula

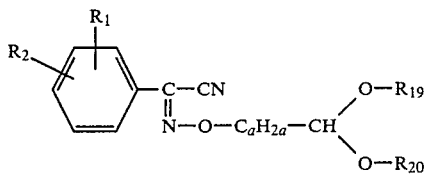

wherein
$R_1$ is hydrogen, methyl, methoxy, chlorine, cyano or trifluoromethyl,
$R_2$ is hydrogen or chlorine, or
$R_2$ is hydrogen or chlorine, or
$R_1$ and $R_2$ taken together is —CH=CH—CH=CH— attached to adjacent carbon atoms in the ring,
$a$ is 1 or 2, and
$R_{19}$ and $R_{20}$ are each methyl or ethyl, or
$R_{19}$ and $R_{20}$ taken together is $C_2$–$C_7$ alkylene having 2 or 3 carbon atoms in its principal chain,
in an amount sufficient to protect sorghum, rice or barley against injury from said herbicide.

8. A composition according to claim 7 in which the herbicide is an s-triazine.

9. A composition according to claim 8 in which the herbicide is 2,4-bis(isopropylamino)-6-methylthio-s-triazine.

10. A composition according to claim 9 in which the herbicide is 4-ethylamino-6-tert.butylamino-2-chloro-s-triazine.

11. A composition according to claim 7 in which the herbicide is a phenoxyphenoxypropionate.

12. A composition according to claim 11 in which the herbicide is α-[4-(p-trifluoromethylphenoxy)-phenoxy]-propionic acid n-butoxyethyl ester.

13. A composition according to claim 7 in which the herbicide is a haloacetanilide.

14. A composition according to claim 13 in which the herbicide is N-[3'-methoxyprop-(2')-yl]-2-methyl-6-ethylchloroacetanilide.

15. A composition according to claim 13 in which the herbicide is N-methoxymethyl-2,6-diethyl-chloroacetanilide.

16. A composition according to claim 13 in which the herbicide is N-ethoxymethyl-2-methyl-6-ethyl-chloroacetanilide.

17. A composition according to claim 13 in which the herbicide is N-[3'-methoxyprop-(2')-yl]-2,6-dimethyl-chloroacetanilide.

18. A composition according to claim 13 in which the herbicide is N-(2'-n-propoxyethyl)-2,6-diethyl-chloroacetanilide.

19. A composition according to claim 14 in which the herbicide is N-(n-butoxymethyl)-2,6-diethyl-chloroacetanilide.

20. A composition according to claim 7 wherein in the formula $R_1$ is hydrogen and $R_2$ is hydrogen or chlorine.

21. A composition according to claim 20 in which the compound is phenylacetonitrile oxime-(2',2'-dimethoxyethyl) ether.

22. A composition according to claim 20 in which the compound is phenylacetonitrile oxime-(2'-ethylenedioxyethyl) ether.

23. A composition according to claim 20 in which the compound is phenylacetonitrile oxime-(2'-propylenedioxyethyl) ether.

24. A composition according to claim 20 in which the compound is 2-chlorophenylacetonitrile oxime-[2'-(2'',2''-dimethyl-propylenedioxy)-ethyl] ether.

25. In the method of controlling weeds in sorghum, rice and barley crop cultures where a 1,3,5-triazine, haloacetanilide or phenoxyphenoxypropionate herbicide is applied to the habitat of said weeds, the improvement comprising applying to said habitat, in sufficient amount to prevent injury to the crop, a compound of the formula

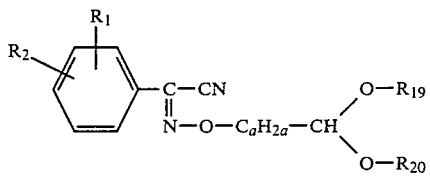

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
$a$ is 1 or 2, and
$R_{19}$ and $R_{20}$ are each methyl or ethyl, or
$R_{19}$ and $R_{20}$ taken together is $C_2$–$C_7$ alkylene having 2 or 3 carbon atoms in its principal chain.

26. The improvement of claim 25 in which the herbicide is an s-triazine.

27. The improvement of claim 26 in which the herbicide is 2,4-bis(isopropylamino)-6-methylthio-s-triazine.

28. The improvement of claim 26 in which the herbicide is 4-ethylamino-6-tert.butylamino-2-chloro-s-triazine.

29. The improvement of claim 26 in which the herbicide is 2-ethylamino-4-isopropylamino6-methylthio-s-triazine.

30. The improvement of claim 26 in which the herbicide is 2-ethylamino-4-(1,2-dimethyl-n-propylamino)-6-methylthio-s-triazine.

31. The improvement of claim 25 in which the herbicide is a phenoxyphenoxypropionate.

32. The improvement of claim 31 in which the herbicide is α-[4-(p-trifluoromethylphenoxy)-phenoxy]-propionic acid n-butoxy-ethyl ester.

33. The improvement of claim 25 in which the herbicide is a haloacetanilide.

34. The improvement of claim 33 in which the herbicide is N-[3'-methoxyprop-(2')-yl]-2-methyl-6-ethyl-chloroacetanilide.

35. The improvement of claim 33 in which the herbicide is N-methoxymethyl-2,6-diethyl-chloroacetanilide.

36. The improvement of claim 33 in which the herbicide is N-ethoxymethyl-2-methyl-6-ethyl-chloroacetanilide.

37. The improvement of claim 33 in which the herbicide is N-[3'-methoxyprop-(2'-)-yl]-2,6-dimethyl-chloroacetanilide.

38. The improvement of claim 33 in which the herbicide is N-(2'-n-propoxyethyl)-2,6-diethyl-chloroacetanilide.

39. The improvement of claim 33 in which the herbicide is N-(n-butoxymethyl)-2,6-diethyl-chloroacetanilide.

40. The improvement of claim 25 in which in the formula of the compound to prevent injury to the crop $R_1$ is hydrogen and $R_2$ is hydrogen or chlorine.

41. The improvement of claim 40 in which the compound is phenylacetonitrile oxime-(2',2'-dimethoxyethyl) ether.

42. The improvement of claim 40 in which the compound is phenylacetonitrile oxime-(2'-ethylenedioxyethyl) ether.

43. The improvement of claim 40 in which the compound is phenylacetonitrile oxime-(2'-propylenedioxyethyl) ether.

44. The improvement according to claim 40 in which the compound is 2-chlorophenylacetonitrile oxime-[2'-(2'',2''-dimethylpropylenedioxy)-ethyl] ether.

45. A method for sorghum, rice and barley crops from injury arising from the action of a 1,3,5-triazine, haloacetanilide or phenoxyphenoxypropionate herbicide, said method comprising applying to the soil, in the rows of seed prior to treatment with said herbicide, a crop protecting amount of a compound of the formula

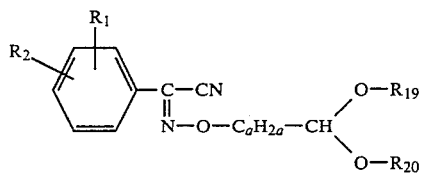

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$-$C_7$ alkylene having 2 or 3 carbon atoms in its principal chain.

46. A method according to claim 45 in which the herbicide is an s-triazine.

47. A method according to claim 46 in which the herbicide is 2,4-bis(isopropylamino)-6-methylthio-s-triazine.

48. A method according to claim 46 in which the herbicide is 2-ethylamino-4-isopropylamino-6-methylthio-s-triazine.

49. A method according to claim 46 in which the herbicide is 2-ethylamino-4-(1,2-dimethyl-n-propyl)-6-methylthio-s-triazine.

50. A method according to claim 45 in which the herbicide is a phenoxyphenoxypropionate.

51. A method according to claim 50 in which the herbicide is α-[4-(p-trifluoromethylphenoxy)-phenoxy]-propionic acid n-butoxyethyl ester.

52. A method according to claim 45 in which the herbicide is a haloacetanilide.

53. A method according to claim 52 in which the herbicide is N-[3'-methoxyprop-(2')-yl]-2-methyl-6-ethyl-chloroacetanilide.

54. A method according to claim 52 in which the herbicide is N-methoxymethyl-2,6-diethyl-chloroacetanilide.

55. A method according to claim 52 in which the herbicide is N-ethoxymethyl-2-methyl-6-ethyl-chloroacetanilide.

56. A method according to claim 52 in which the herbicide is N-[3'-methoxyprop-(2')-yl]-2,6-dimethyl-chloroacetanilide.

57. A method according to claim 52 in which the herbicide is N-(2'-n-propoxyethyl)-2,6-diethyl-chloroacetanilide.

58. A method according to claim 52 in which the herbicide is N-(n-butoxymethyl)-2,6-diethyl-chloroacetanilide.

59. A method according to claim 45 wherein in the formula of the crop protecting compound $R_1$ is hydrogen and $R_2$ is hydrogen or chlorine.

60. A method according to claim 59 in which the compound is phenylacetonitrile oxime-2',2'-dimethoxyethyl) ether.

61. A method according to claim 59 in which the compound is phenylacetonitrile oxime-(2'-ethylenedioxyethyl) ether.

62. A method according to claim 59 in which the compound is phenylacetonitrile oxime-(2'-propylenedioxyethyl) ether.

63. A method according to claim 59 in which the compound is 2-chlorophenylacetonitrile oxime-[2'-(2'',2''-dimethylpropylenedioxy)-ethyl] ether.

64. A method for protecting sorghum, rice and barley crops from injury caused by application of a 1,3,5-triazine, haloacetanilide or phenoxyphenoxypropionate herbicide, said method comprising applying to the crop seeds a crop protecting amount of a compound of the formula

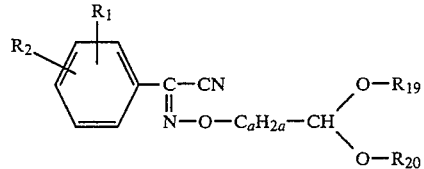

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$-$C_7$ alkylene having 2 or 3 carbon atoms in its principal chain.

65. A method according to claim 64 in which the herbicide is an s-triazine.

66. A method according to claim 65 in which the herbicide is 2,4-bis(isopropylamino)-6-methylthio-s-triazine.

67. A method according to claim 65 in which the herbicide is 4-ethylamino-6-tert.butylamino-2-chloro-s-triazine.

68. A method according to claim 65 in which the herbicide is 2-ethylamino-4-isopropylamino-6-methylthio-s-triazine.

69. A method according to claim 65 in which the herbicide is 2-ethylamino-4-(1,2-dimethyl-n-propylamino)-6-methylthio-s-triazine.

70. A method according to claim 64 in which the herbicide is a phenoxyphenoxypropionate.

71. A method according to claim 70 in which the herbicide is α-[4-(p-trifluoromethylphenoxy)-phenoxy]-propionic acid n-butoxy-ethyl ester.

72. A method according to claim 64 in which the herbicide is a haloacetanilide.

73. A method according to claim 72 in which the herbicide is N-[3'-methoxyprop-(2')-yl]-2-methyl-6-ethylchloroacetanilide.

74. A method according to claim 72 in which the herbicide is N-methoxymethyl-2,6-diethyl-chloroacetanilide.

75. A method according to claim 72 in which the herbicide is N-ethoxymethyl-2-methyl-6-ethyl-chloroacetanilide.

76. A method according to claim 72 in which the herbicide is N-[3'-methoxyprop-(2')-yl]-2,6-dimethyl-chloroacetanilide.

77. A method according to claim 72 in which the herbicide is N-(2'-n-propoxyethyl)-2,6-diethyl-chloroacetanilide.

78. A method according to claim 72 in which the herbicide is N-(n-butoxymethyl)-2,6-diethyl-chloroacetanilide.

79. A method according to claim 64 wherein in the formula of the crop protecting compound $R_1$ is hydrogen and $R_2$ is hydrogen or chlorine.

80. A method according to claim 79 in which the compound is phenylacetonitrile oxime-(2',2'-dimethoxyethyl) ether.

81. A method according to claim 79 in which the compound is phenylacetonitrile oxime-(2'-ethylenedioxyethyl) ether.

82. A method according to claim 79 in which the compound is phenylacetonitrile oxime-(2'-propylenedioxyethyl) ether.

83. A method according to claim 79 in which the compound is 2-chlorophenylacetonitrile oxime-[2'-(2'',2''-dimethylpropylenedioxy)-ethyl] ether.

84. A method for protecting rice from injury caused by application of a 1,3,5-triazine or haloacetanilide herbicide, said method comprising dipping the roots of rice seedlings into a solution comprising a crop protecting effective amount of a compound of the formula

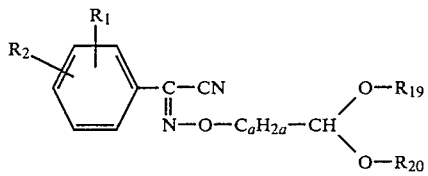

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$–$C_7$ alkylene having 2 or 3 carbon atoms in its principal chain.

85. A method according to claim 84 in which the herbicide is an s-triazine.

86. A method according to claim 85 in which the herbicide is 2-ethylamino-4-(1,2-dimethyl-n-propylamino)-6-methylthio-s-triazine.

87. A method accotding to claim 84 in which the herbicide is a haloacetanilide.

88. A method according to claim 87 in which the herbicide is N-(2'-n-propoxyethyl)-2,6-diethyl-chloroacetanilide.

89. A method according to claim 87 in which the herbicide is N-[3'-methoxyprop-(2')-yl]-2-methyl-6-ethyl-chloroacetanilide.

90. A method according to claim 84 wherein in the formula of the crop protecting compound $R_1$ is hydrogen and $R_2$ is hydrogen or chlorine.

91. A method according to claim 90 in which the compound is phenylacetonitrile oxime-(2',2'-dimethoxyethyl) ether.

92. A method according to claim 90 in which the compound is phenylacetonitrile oxime-(2'-ethylenedioxyethyl) ether.

93. A method according to claim 90 in which the compound is phenylacetonitrile oxime-(2'-propylenedioxyethyl) ether.

94. A method according to claim 90 in which the compound is 2-chlorophenylacetonitrile oxime-[2'-(2'',2''-dimethyl-propylenedioxy)-ethyl] ether.

95. A method for selectively controlling weeds in sorghum, rice and barley crop cultures which comprises applying to a culture of said crop grown from seed treated with a safening amount of a compound of the formula

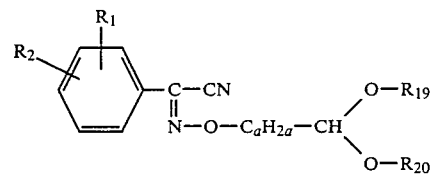

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$–$C_7$ alkylene having 2 or 3 carbon atoms in its principal chain,
an effective amount of a 1,3,5-triazine, haloacetanilide or phenoxyphenoxypropionate herbicide.

96. A method according to claim 95 in which the herbicide is an s-triazine.

97. A method according to claim 96 in which the herbicide is 2,4-bis(isopropylamino)-6-methylthio-s-triazine.

98. A.method according to claim 96 in which the herbicide is 2-ethylamino-4-(1,2-dimethyl-n-propylamino)-6-methylthio-s-triazine.

99. A method according to claim 95 in which the herbicide is a phenoxyphenoxypropionate.

100. A method according to claim 95 in which the herbicide is a haloacetanilide.

101. A method according to claim 100 in which the herbicide is N-[3'-methoxyprop-(2')-yl]-2-methyl-6-ethylchloroacetanilide.

102. A method according to claim 100 in which the herbicide is N-methoxymethyl-2,6-diethyl-chloroacetanilide.

103. A method according to claim 100 in which the herbicide is N-ethoxymethyl-2-methyl-6-ethyl-chloroacetanilide.

104. A method according to claim 100 in which the herbicide is N-[3'-methoxyprop-(2')-yl]-2,6-dimethyl-chloroacetanilide.

105. A method according to claim 100 in which the herbicide is N-(2'-n-propoxyethyl)-2,6-diethyl-chloroacetanilide.

106. A method according to claim 100 in which the herbicide is N-(n-butoxymethyl)-2,6-diethyl-chloroacetanilide.

107. A method according to claim 95 wherein in the formula of the safening compound $R_1$ is hydrogen and $R_2$ is hydrogen or chlorine.

108. A method according to claim 107 in which the compound is phenylacetonitrile oxime-(2',2'-dimethoxyethyl) ether.

109. A method according to claim 107 in which the compound is phenylacetonitrile oxime-(2'-ethylenedioxyethyl) ether.

110. A method according to claim 107 in which the compound is phenylacetonitrile oxime-(2'-propylenedioxyethyl) ether.

111. A method according to claim 107 in which the compound is 2-chlorophenylacetonitrile oxime-[2'-(2'',2''-dimethylpropylenedioxy)-ethyl] ether.

112. A method for selectively controlling weeds in rice cultures which comprises applying to a rice culture grown from plants whose roots have been dipped in a solution containing a safening amount of a compound of the formula

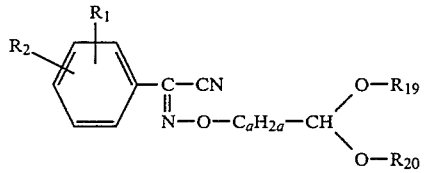

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$–$C_7$ alkylene having 2 or 3 carbon atoms in its principal chain,
an effective amount of a 1,3,5-triazine or haloacetanilide herbicide.

113. A method according to claim 112 in which the herbicide is an s-triazine.

114. A method according to claim 113 in which the herbicide is 2-ethylamino-4-(1,2-dimethyl-n-propylamino)-6-methylthio-s-triazine.

115. A method according to claim 112 in which the herbicide is a haloacetanilide.

116. A method according to claim 115 in which the herbicide is N-[3'-methoxyprop-(2')-yl]-2-methyl-6-ethylchloroacetanilide.

117. A method according to claim 115 in which the herbicide is N-(2'-n-propoxyethyl)-2,6-diethyl-chloroacetanilide.

118. A method according to claim 115 wherein in the formula of the safening compound $R_1$ is hydrogen and $R_2$ is hydrogen or chlorine.

119. A method according to claim 118 in which the compound is phenylacetonitrile oxime-(2',2'-dimethoxyethyl) ether.

120. A method according to claim 118 in which the compound is phenylacetonitrile oxime-(2'-ethylenedioxyethyl) ether.

121. A method according to claim 118 in which the compound is phenylacetonitrile oxime-(2'-propylenedioxyethyl) ether.

122. A method according to claim 118 in which the compound is 2-chlorophenylacetonitrile oxime-[2'-(2'',2''-dimethylpropylenedioxy)-ethyl] ether.

123. Sorghum, rice and barley seed, the plants grown from which are resistant to injury caused by application of a 1,3,5-triazine, haloacetanilide or phenoxyphenoxypropionate herbicide, said seed having been coated with a safening amount of a compound of the formula

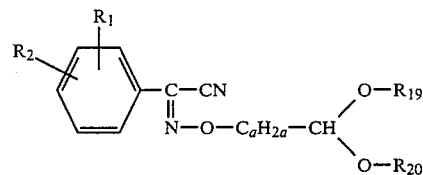

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$–$C_7$ alkylene having 2 or 3 carbon atoms in its principal chain.

124. Seed according to claim 123 in which the herbicide is an s-triazine.

125. Seed according to claim 124 in which the herbicide is 2,4-bis(isopropylamino)-6-methylthio-s-triazine.

126. Seed according to claim 124 in which the herbicide is 2-ethylamino-4-(1,2-dimethyl-n-propylamino)-6-methylthio-s-triazine.

127. Seed according to claim 123 in which the herbicide is a phenoxyphenoxypropionate.

128. Seed according to claim 123 in which the herbicide is a haloacetanilide.

129. Seed according to claim 128 in which the herbicide is N-[3'-methoxyprop-(2')-yl]-2-methyl-6-ethyl-chloroacetanilide.

130. Seed according to claim 128 in which the herbicide is N-methoxymethyl-2,6-diethyl-chloroacetanilide.

131. Seed according to claim 128 in which the herbicide is N-ethoxymethyl-2-methyl-6-ethyl-chloroacetanilide.

132. Seed according to claim 128 in which the herbicide is N-[3'-methoxyprop-(2')-yl]-2,6-dimethyl-chloroacetanilide.

133. Seed according to claim 128 in which the herbicide is N-(2'-n-propoxyethyl)-2,6-diethyl-chloroacetanilide.

134. Seed according to claim 128 in which the herbicide is N-(n-butoxymethyl)-2,6-diethyl-chloroacetanilide.

135. Seed according to claim 123 wherein in the formula of the crop protecting compound $R_1$ is hydrogen and $R_2$ is hydrogen or chlorine.

136. Seed according to claim 135 in which the compound is phenylacetonitrile oxime-(2',2'-dimethoxyethyl) ether.

137. Seed according to claim 135 in which the compound is phenylacetonitrile oxime-(2'-ethylendioxyethyl) ether.

138. Seed according to claim 135 in which the compound is phenylacetonitrile oxime-(2'-propylenedioxyethyl) ether.

139. Seed according to claim 135 in which the compound is 2-chlorophenylacetonitrile oxime-[2'-(2'',2''-dimethylpropylenedioxy)-ethyl] ether.

140. A method for protecting sorghum from injury caused by application of a 1,3,5-triazine or haloacetanilide herbicide, said method comprising treating sorghum seed with an effective amount of a compound of the formula

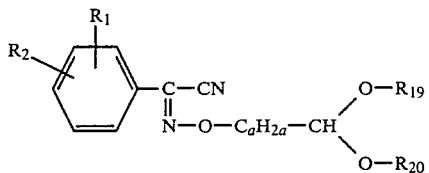

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$-$C_7$ alkylene having 2 or 3 carbon atoms in its principal chain.

141. A method according to claim 140 in which the herbicide is an s-triazine.

142. A method according to claim 141 in which the herbicide is 2,4-bis(isopropylamino)-6-methylthio-s-triazine.

143. A method according to claim 140 in which the herbicide is a haloacetanilide.

144. A method according to claim 143 in which the herbicide is N-[3'-methoxyprop-(2')-yl]-2-methyl-6-ethylchloroacetanilide.

145. A method according to claim 143 in which the herbicide is N-methoxymethyl-2,6-diethyl-chloroacetanilide.

146. A method according to claim 143 in which the herbicide is N-ethoxymethyl-2-methyl-6-ethyl-chloroacetanilide.

147. A method according to claim 143 in which the herbicide is N-[3'-methoxyprop-(2')-yl]-2,6-dimethyl-chloroacetanilide.

148. A method according to claim 143 in which the herbicide is N-(2'-n-propoxyethyl)-2,6-diethyl-chloracetanilide.

149. A method according to claim 143 in which the herbicide is N-(n-butoxymethyl)-2,6-diethyl-chloroacetanilide.

150. A method according to claim 140 wherein in the formula of the crop protecting compound $R_1$ is hydrogen and $R_2$ is hydrogen or chlorine.

151. A method according to claim 150 in which the compound is phenylacetonitrile oxime-(2',2'-dimethoxyethyl) ether.

152. A method according to claim 150 in which the compound is phenylacetonitrile oxime-(2'-ethylenedioxyethyl) ether.

153. A method according to claim 150 in which the compound is phenylacetonitrile oxime-(2'-propylenedioxyethyl) ether.

154. A method according to claim 150 in which the compound is 2-chlorophenylacetonitrile oxime-[2'-(2'',2''-dimethyl-propylenedioxy)-ethyl] ether.

155. A method for selectively controlling weeds in sorghum cultures which comprises applying to a sorghum culture grown from seed treated with a safening amount of a compound of the formula

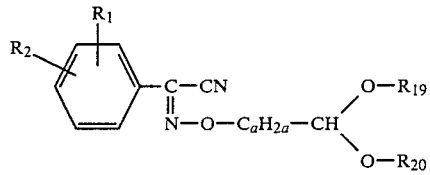

wherein
$R_1$ is hydrogen, methyl, methoxy, chlorine, cyano or trifluoromethyl,
$R_2$ is hydrogen or chlorine, or
$R_1$ and $R_2$ taken together is —CH=CH—CH=CH— attached to adjacent carbon atoms in the ring,
a is 1 or 2, and
$R_{19}$ and $R_{20}$ are each methyl or ethyl, or
$R_{19}$ and $R_{20}$ taken together is $C_2$-$C_7$ alkylene having 2 or 3 carbon atoms in its principal chain,
an effective amount of a 1,3,5-triazine or haloacetanilide herbicide.

156. A method according to claim 141 in which the herbicide is an s-triazine.

157. A method according to claim 156 in which the herbicide is 2,4-bis(isopropylamino)-6-methylthio-s-triazine.

158. A method according to claim 141 in which the herbicide is a haloacetanilide.

159. A method according to claim 158 in which the herbicide is N-[3'-methoxyprop-(2')-yl]-2-methyl-6-ethyl-chloroacetanilide.

160. A method according to claim 158 in which the herbicide is N-methoxymethyl-2,6-diethyl-chloroacetanilide.

161. A method according to claim 158 in which the herbicide is N-ethoxymethyl-2-methyl-6-ethyl-chloroacetanilide.

162. A method according to claim 158 in which the herbicide is N-[3'-methoxyprop-(2')-yl]-2,6-dimethyl-chloroacetanilide.

163. A method according to claim 158 in which the herbicide is N-(2'-n-propoxyethyl)-2,6-diethyl-chloroacetanilide.

164. A method according to claim 158 in which the herbicide is N-(n-butoxymethyl)-2,6-diethyl-chloroacetanilide.

165. A method according to claim 155 wherein in the formula of the safening compound $R_1$ is hydrogen and $R_2$ is hydrogen or chlorine.

166. A method according to claim 165 in which the compound is phenylacetonitrile oxime-(2',2'-dimethoxyethyl) ether.

167. A method according to claim 165 in which the compound is phenylacetonitrile oxime-(2'-ethylenedioxyethyl) ether.

168. A method according to claim 165 in which the compound is phenylacetonitrile oxime-(2'-propylenedioxyethyl) ether.

169. A method according to claim 165 in which the compound is 2-chlorophenylacetonitrile oxime-[2'-(2'',2''-dimethyl-propylenedioxy)-ethyl] ether.

* * * * *